United States Patent
Jones et al.

(10) Patent No.: US 8,882,813 B2
(45) Date of Patent: Nov. 11, 2014

(54) LOCKING MECHANISMS AND ASSOCIATED METHODS

(75) Inventors: Robert J. Jones, Austin, TX (US); Timothy J. Leak, Cedar Park, TX (US)

(73) Assignee: SpineSmith Partners, L.P., Austin, TX (US)

( * ) Notice: Subject to any disclaimer, the term of this patent is extended or adjusted under 35 U.S.C. 154(b) by 1234 days.

(21) Appl. No.: 12/044,186

(22) Filed: Mar. 7, 2008

(65) Prior Publication Data

US 2009/0105831 A1  Apr. 23, 2009

Related U.S. Application Data

(60) Provisional application No. 60/981,358, filed on Oct. 19, 2007.

(51) Int. Cl.
| | |
|---|---|
| *A61B 17/80* | (2006.01) |
| *A61F 2/44* | (2006.01) |
| *A61B 17/70* | (2006.01) |
| *A61F 2/30* | (2006.01) |

(52) U.S. Cl.
CPC ..... *A61F 2/4465* (2013.01); *A61F 2002/30604* (2013.01); *A61F 2002/30578* (2013.01); *A61F 2002/4475* (2013.01); *A61B 17/7059* (2013.01); *A61F 2/30744* (2013.01); *A61F 2002/30672* (2013.01); *A61F 2002/30517* (2013.01); *A61B 17/8042* (2013.01); *A61F 2002/30892* (2013.01); *A61F 2220/0025* (2013.01)
USPC ............................. 606/289; 623/17.16

(58) Field of Classification Search
USPC .............. 606/60, 71, 280, 281, 286, 289; 623/17.11–17.16
See application file for complete search history.

(56) References Cited

U.S. PATENT DOCUMENTS

| | | | |
|---|---|---|---|
| 2,825,329 | A | 3/1958 | Caesar |
| 3,528,085 | A | 9/1970 | Reynolds, Jr. |
| 3,534,731 | A | 10/1970 | Muller |
| 3,842,825 | A | 10/1974 | Wagner |
| 4,013,071 | A | 3/1977 | Rosenberg |
| 4,388,921 | A | 6/1983 | Sutter et al. |
| 4,432,358 | A | 2/1984 | Fixel |
| 4,488,543 | A | 12/1984 | Tornier |
| 4,794,918 | A | 1/1989 | Wolter |
| 5,127,914 | A | 7/1992 | Calderale et al. |
| 5,364,399 | A | 11/1994 | Lowery et al. |
| 5,534,027 | A | 7/1996 | Hodorek |

(Continued)

FOREIGN PATENT DOCUMENTS

| | | |
|---|---|---|
| EP | 455255 | 11/1991 |
| EP | 599640 | 6/1994 |

OTHER PUBLICATIONS

Reliant Anterior Cervical Plating System—Surgical Technique, pp. 10-11, copyright 2006.

*Primary Examiner* — Anu Ramana
(74) *Attorney, Agent, or Firm* — Winstead PC

(57) ABSTRACT

A method and apparatus is provided for use with a surgical implant to secure fasteners, such as bone screws or pins. An anti-backout mechanism is used to preventing migration of the fasteners after the implant is installed. In one example, an anti-backout mechanism includes a locking plate having a locked position and an unlocked position. The locking plate has one or more protrusions that are configured to prevent migration the fasteners when the locking plate is in the locked position.

3 Claims, 15 Drawing Sheets

(56) References Cited

U.S. PATENT DOCUMENTS

| | | | |
|---|---|---|---|
| 5,549,612 A | 8/1996 | Yapp et al. | |
| 5,569,250 A * | 10/1996 | Sarver et al. | 606/281 |
| 5,616,144 A | 4/1997 | Yapp et al. | |
| 5,681,311 A | 10/1997 | Foley et al. | |
| 5,713,900 A | 2/1998 | Benzel et al. | |
| 5,800,433 A | 9/1998 | Benzel et al. | |
| 5,888,223 A | 3/1999 | Bray | |
| 5,951,558 A * | 9/1999 | Fiz | 606/70 |
| 6,139,550 A | 10/2000 | Michelson | |
| 6,152,927 A | 11/2000 | Farris et al. | |
| 6,193,721 B1 | 2/2001 | Michelson | |
| 6,228,087 B1 | 5/2001 | Fenaroli et al. | |
| 6,235,034 B1 | 5/2001 | Bray | |
| 6,306,139 B1 | 10/2001 | Fuentes | |
| 6,361,537 B1 | 3/2002 | Anderson | |
| 6,383,186 B1 | 5/2002 | Michelson | |
| 6,413,259 B1 | 7/2002 | Lyons et al. | |
| 6,503,250 B2 | 1/2003 | Paul | |
| 6,592,586 B1 | 7/2003 | Michelson | |
| 6,602,255 B1 | 8/2003 | Campbell et al. | |
| 6,620,163 B1 | 9/2003 | Michelson | |
| 6,652,525 B1 | 11/2003 | Assaker et al. | |
| 6,730,127 B2 * | 5/2004 | Michelson | 623/17.16 |
| 6,755,833 B1 | 6/2004 | Paul et al. | |
| 6,793,658 B2 | 9/2004 | LeHuec et al. | |
| 6,893,444 B2 | 5/2005 | Orbay | |
| 6,936,050 B2 | 8/2005 | Michelson | |
| 6,936,051 B2 | 8/2005 | Michelson | |
| 6,945,973 B2 | 9/2005 | Bray | |
| 6,972,019 B2 | 12/2005 | Michelson | |
| 7,025,769 B1 | 4/2006 | Ferree | |
| 7,033,394 B2 | 4/2006 | Michelson | |
| 7,041,105 B2 | 5/2006 | Michelson | |
| 7,172,627 B2 | 2/2007 | Fiere et al. | |
| 7,846,207 B2 * | 12/2010 | Lechmann et al. | 623/17.11 |
| 7,862,616 B2 * | 1/2011 | Lechmann et al. | 623/17.11 |
| 2002/0128655 A1 | 9/2002 | Michelson | |
| 2003/0060828 A1 | 3/2003 | Michelson | |
| 2003/0149434 A1 | 8/2003 | Paul | |
| 2005/0021032 A1 | 1/2005 | Koo | |
| 2005/0101960 A1 | 5/2005 | Fiere et al. | |
| 2006/0085071 A1 | 4/2006 | Lechmann et al. | |
| 2006/0149253 A1 | 7/2006 | Doubler et al. | |
| 2006/0149255 A1 | 7/2006 | Doubler et al. | |
| 2006/0200146 A1 | 9/2006 | Doubler et al. | |
| 2006/0229620 A1 | 10/2006 | Rothman et al. | |
| 2008/0306596 A1 | 12/2008 | Jones et al. | |
| 2009/0105830 A1 | 4/2009 | Jones et al. | |

* cited by examiner

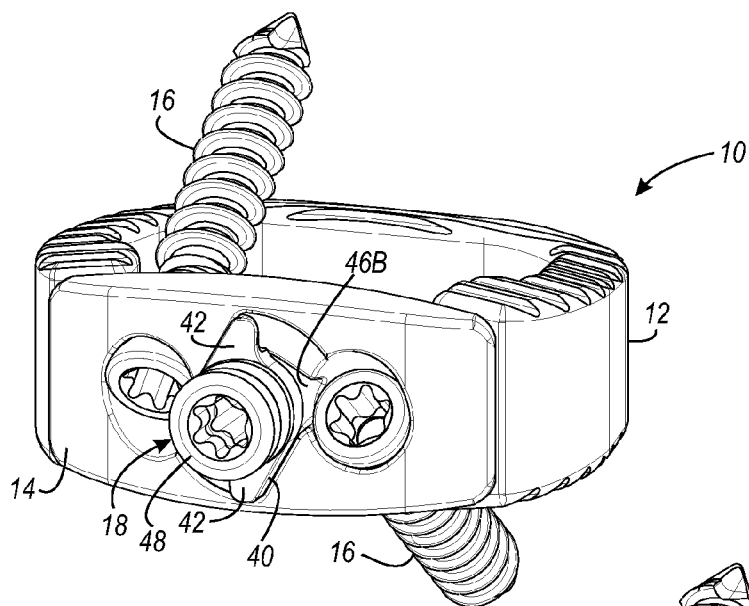
FIG. 3
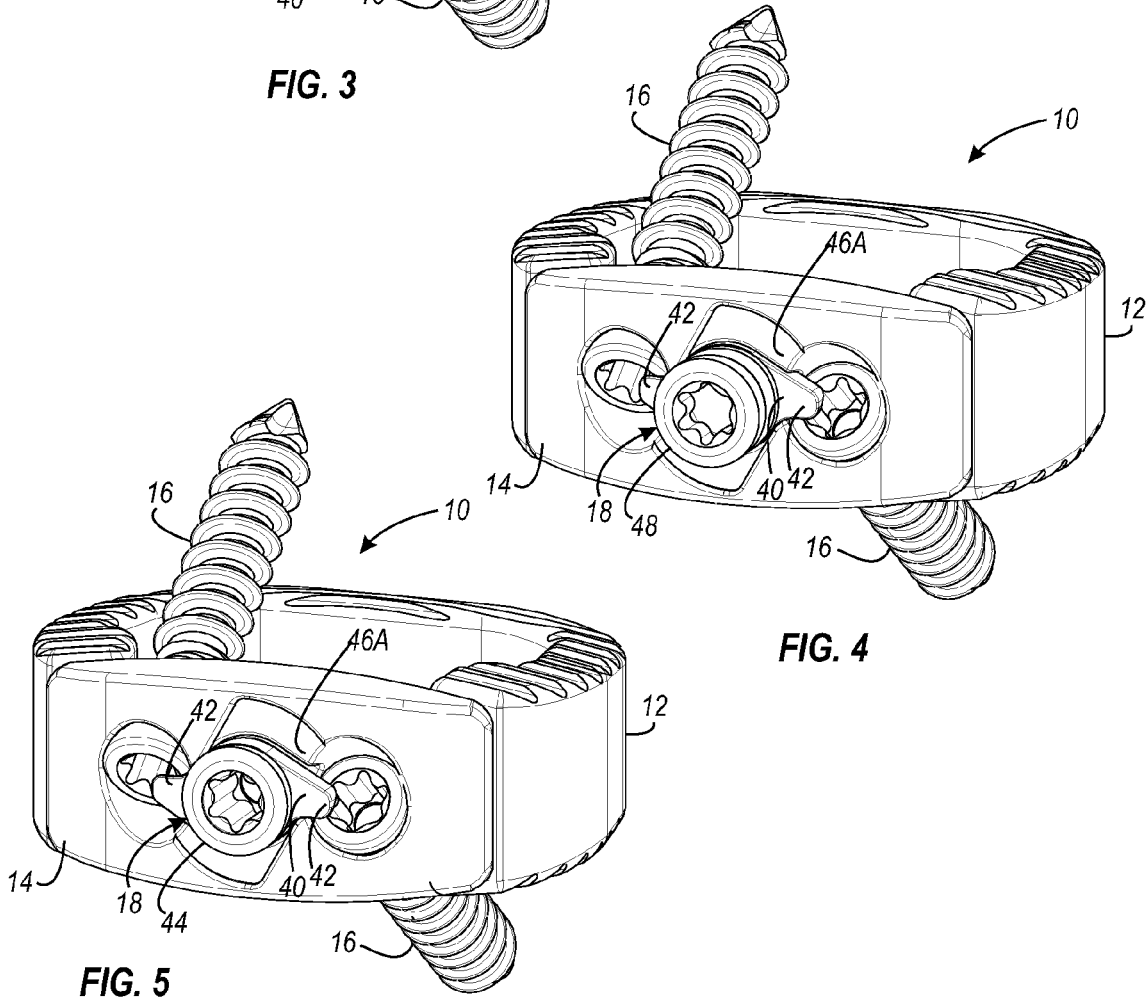
FIG. 4
FIG. 5

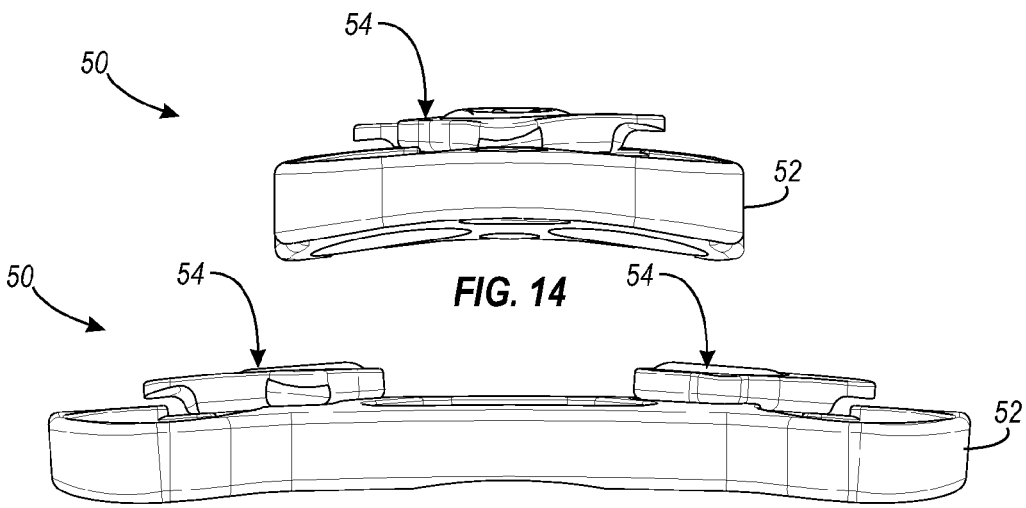
FIG. 14
FIG. 15
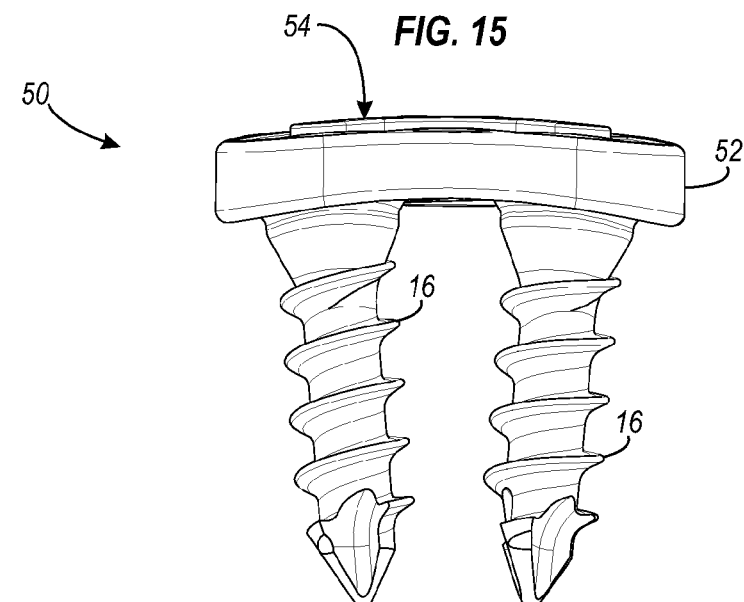
FIG. 16
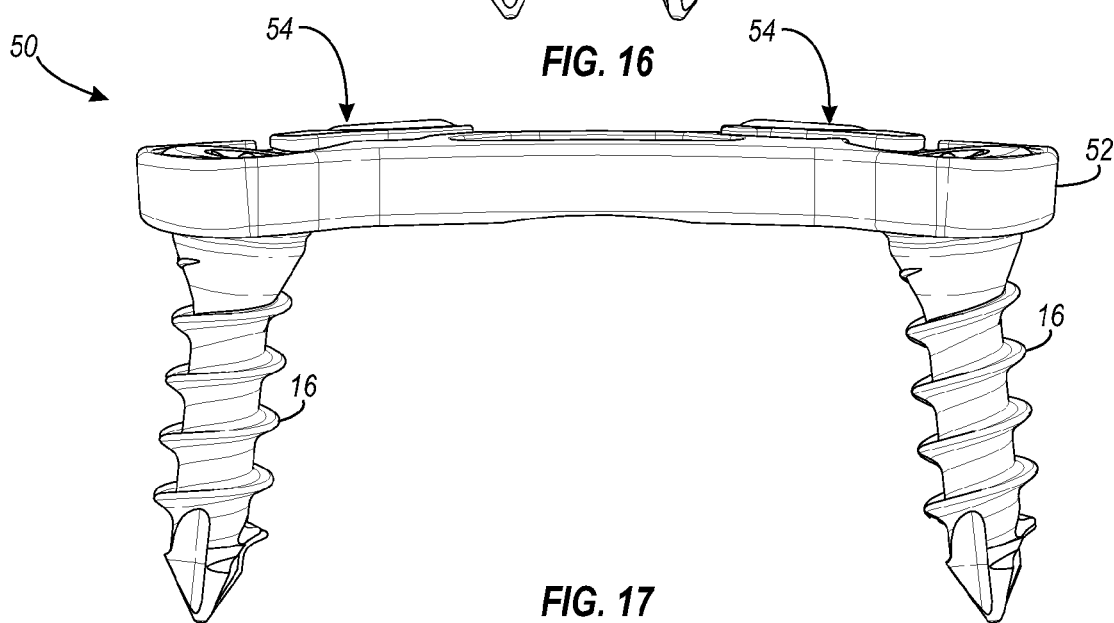
FIG. 17

LOCKING MECHANISMS AND ASSOCIATED METHODS

CROSS REFERENCE TO RELATED APPLICATIONS

This application claims priority under 35 U.S.C. §119, commonly owned U.S. provisional patent application No. 60/981,358, filed on Oct. 19, 2007, entitled "LOCKING MECHANISMS AND ASSOCIATED METHODS," which is incorporated by reference herein.

FIELD OF THE INVENTION

This invention relates to the field of surgical implants. In particular, this invention is drawn to anti-backout, or locking mechanisms for surgical implants.

BACKGROUND OF THE INVENTION

It is common for surgical implants to be secured in place using screws or other fasteners. One problem with securing surgical implants with screws or other fasteners relates to fastener migration. After fixation, fasteners may tend to gradually become loose, which is undesirable. In addition, as fasteners become loose, they may protrude outward and can be a source of discomfort and potentially cause trauma to nearby tissue.

Attempts to address these problems have resulted in various types of anti-backout or locking mechanism. However, prior art locking mechanisms present various disadvantages. One problem with some prior art locking mechanisms is that they are cumbersome to a surgeon. Some locking mechanisms require a surgeon to introduce and assemble multiple parts within a patient's body after the implant has been installed. Some locking mechanisms require special tools (e.g., torque wrenches, specialized drivers, etc.) to ensure that they are installed properly. Many prior art locking mechanisms are unnecessarily complex, and therefore expensive and difficult to use.

There is a need for anti-backout mechanisms that function properly, are easy to use, etc. In addition, it is also desired to provide anti-backout mechanisms that are simple and less expensive than other alternatives.

SUMMARY OF THE INVENTION

An apparatus of the invention is provided for a medical device including an implant, one or more fasteners configured to secure the implant in an implanted position, a recess formed in the implant, a movable device coupled to the implant, the movable device having a locked position and an unlocked position, wherein, in the locked position, the movable device is at least partially disposed in the recess, and one or more protrusions extending from the movable device, wherein the one or more protrusions are configured prevent migration of the one or more fasteners when the movable device is in the locked position.

Another embodiment of the invention provides a locking device for a medical device including an implant, a plate rotatably coupled to the implant between a locked and an unlocked position, wherein the range of rotation of the plate is limited, and a threaded fastener rotatably coupled to the plate and threadably coupled to the implant for securing the plate to the implant.

Another embodiment of the invention provides a medical device including a bone plate configured to be positioned in the proximity of two or more bones, a first fastener configured to be fastened to a first bone, a second fastener configured to be fastened to a second bone, a locking device coupled to the bone plate for preventing migration of the first and second fasteners.

Another embodiment of the invention provides an apparatus for use with a medical device having a pre-assembled threaded fastener to prevent the threaded fastener from migrating prior to use of the medical device, the apparatus including a first member configured to couple to the threaded fastener of the medical device, and a second member coupled to the first member, the second member being configured to contact the medical device to prevent the first member and the threaded fastener from turning.

Another embodiment of the invention provides a method of securing a medical device including providing a medical implant having one or more apertures formed for receiving fasteners, providing a rotatable device have a first position and a second position relative to the medical implant, wherein the apertures are accessible when the rotatable device is in the first position, and wherein the apertures are at least partially obstructed when the rotatable device is in the second position, configuring the rotatable device and the medical implant such that a desired amount of friction exists between the rotatable device and the medical implant, implanting the medical implant in a desired position, inserting one or more fasteners through the one or more apertures to fasten the medical implant in the desired position, and rotating the rotatable device from the first position to the second position.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIGS. 3-5 are isometric views illustrating the operation of the anti-backout device shown in FIGS. 1-2.

FIGS. 12-17 show various isometric views of the surgical implant of FIG. 6 in locked and unlocked positions.

DETAILED DESCRIPTION

The present invention relates to locking mechanisms used with surgical implants for use in various medical applications. Numerous types of surgical implants use fasteners such as screws or pins to fix the implant in place. Examples of surgical implants that may secured using fasteners includes bone plates, spinal fusion devices, intervertebral spinal devices, artificial joints, etc. The present invention will be described using several examples of surgical implants, but it should be understood that locking devices of the present invention can be used with any desired implant.

Figure 1:
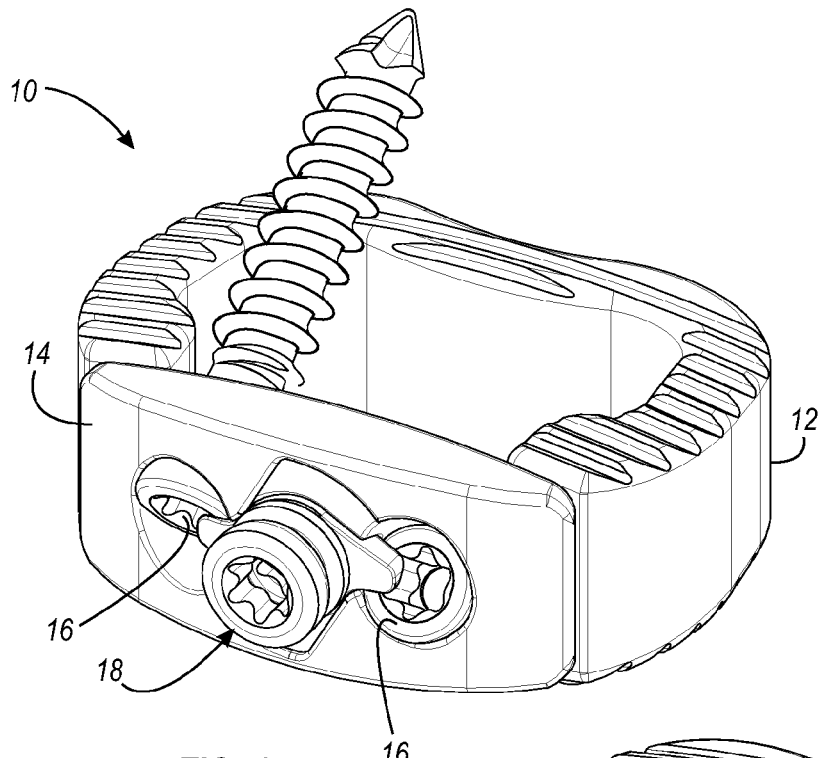
FIG. 1 is an isometric view illustrating one example of an anti-backout device of the present invention.

FIG. 1 is an isometric view of one example of an anti-backout device of the present invention. In this example, the anti-backout device is shown being used with an interbody fusion device, although the anti-backout device may be used with any desired type of surgical implant. FIG. 1 shows a surgical implant 10, including a load bearing device 12, and a retention device 14. FIG. 1 also shows two bone screws 16 and an anti-backout mechanism 18, each of which are described in more detail below.

Figure 2:
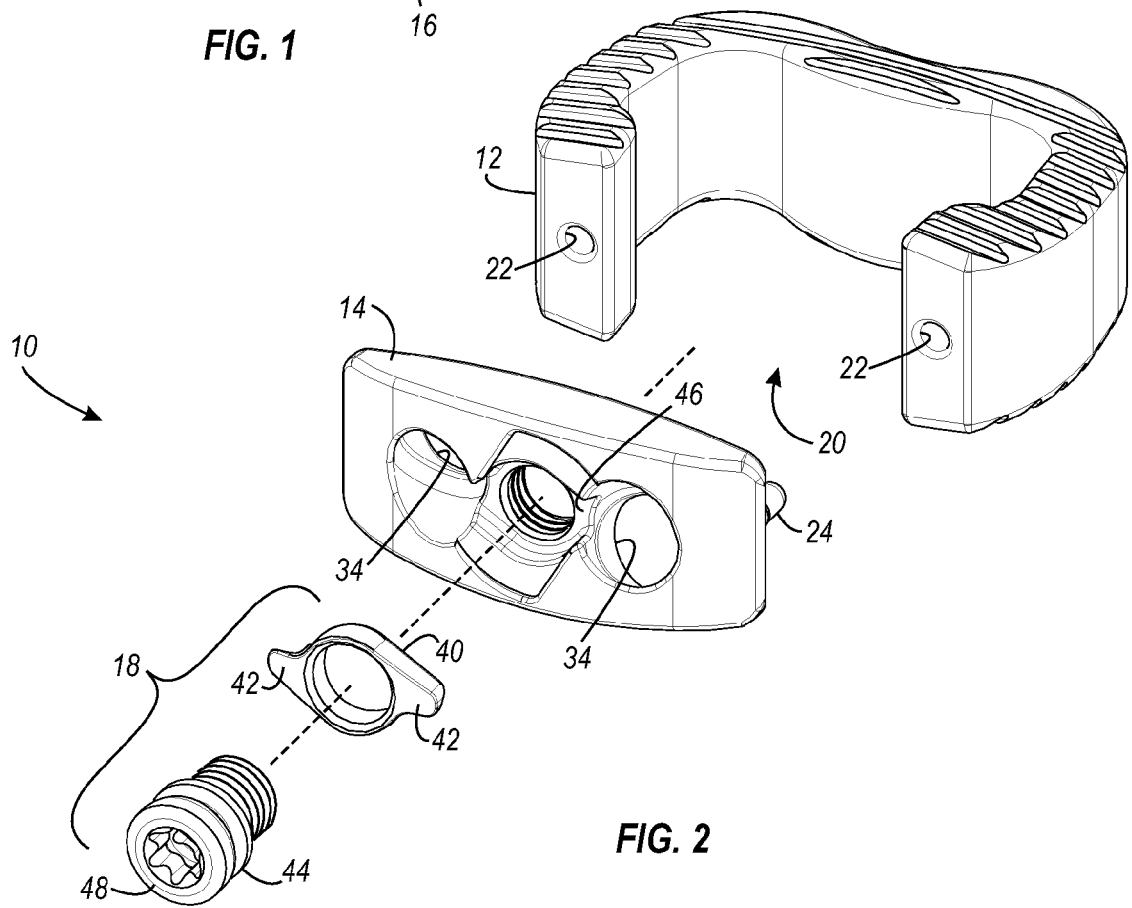
FIG. 2 is an exploded view of the anti-backout device shown in FIG. 1.

FIG. 2 is an exploded view of the surgical implant 10, showing the load bearing device 12, the retention device 14, and the anti-backout mechanism 18 separately. The load bearing device 12 is a generally U-shaped device having an open end 20. The open end defines an opening that allows access to the vertebrae end plates when the load bearing device is installed. The leading edges of the load bearing device 12 include holes 22, which are configured to receive pins 24 extending from the retention device 14. The pins 24 properly align the retention device 14 with the load bearing device 12 and hold the retention device 14 in a desired position, relative to the load bearing device 12.

In the exemplary implant 10 shown in FIG. 2, two holes 34 are formed in the retention device 14, and are adapted to received fasteners, such as bone screws, pegs, etc. In this example, one of the holes 34 is angled down, and the other hole 34 is angled up, such that a first fastener can be secured to the vertebra above the interbody fusion device 10, and a second fastener can be secured to the vertebra below the interbody fusion device 10. The anti-backout device 18 will work regardless of the configuration of the holes 34, though.

FIG. 2 illustrates details of the components of the anti-backout mechanism 18. The anti-backout mechanism 18 includes a locking plate 40. The plate 40 has two opposing protrusions 42 that extend outward from the plate 40. A set screw 44 is configured to extend through an opening formed in the plate 40, and thread into the retention device 14. A recess 46 is formed in the retention device 14 that is adapted to receive the locking plate 40. The set screw 44 includes a head 48 that will shear off when enough torque is applied by a driver. By shearing off the head 48, the surgeon will know that the set screw 44 is tight enough, and it will reduce the profile of the fusion device 10. The retention device 14, locking plate 40, and set screw 44 can be pre-assembled, such that a surgeon will have a single piece that is attached to the load bearing device 12. Once the bone screws are installed, the surgeon needs only to turn the set screw 44 with a driver (the example shown in FIG. 2 shows a star screwdriver, or Torx™ driver) to lock the bone screws in place. When the head 48 shears off, it will stay attached to the driver as the surgeon removes the driver from the patient. More details of the operation of the anti-backout mechanism 18 is described below.

FIGS. 3-5 are isometric views illustrating the operation of the anti-backout mechanism 18 described above. FIG. 3 shows the implant 10 after the bone screws have been installed. Note that the position of the protrusions 42 of the locking plate 40 are such that the openings 34 are not obstructed, allowing a surgeon to install the bone screws 16. As mentioned above, the retention device 14 can come pre-assembled with the anti-backout mechanism in the position shown in FIG. 3. Once the bone screws are in place, the surgeon can use a driver to turn the set screw 44. FIG. 4 shows the implant 10 after the set screw 44 has been turned. In this example, the set screw 44 is rotated clockwise which, in turn, rotates the locking plate 40 approximately 90° until the protrusions 42 obstruct the heads of the bone screws 16. When the locking plate 40 is in this position, the bone screws cannot come out. As shown in FIGS. 3 and 4, the recess 46 has multiple depths. In this example, the recess has a first depth (shown at 46A) and a second deeper depth shown at 46B. As the locking plate 40 is turned, the locking plate 40 will drop from the recess 46A and seat into the deeper recess 46B. One advantage of the invention is that a surgeon will know when the locking mechanism is locked because the surgeon will feel the locking plate 40 drop into the deeper recess while turning the set screw 44 with a driver.

When the locking plate 40 is seated within the deeper recess 46B (FIGS. 4 and 5), the shape of the recess 46 will tend to prevent the locking plate 40 from turning the back the other way. The protrusions 42 prevent the screws 16 from backing out by obstructing the opening 34. In the example shown in FIGS. 3-5, a gap is formed between the protrusions 42 and the heads of the screws 16. In other examples, the protrusions 42 may contact the screws 16. When the surgeon applies the appropriate amount of torque to the set screw 44, the head 48 of the set screw 44 will sheer off, eliminating the need for a torque wrench. This also lessens the profile of the implant. If the implant has to be removed in the future, a surgeon can use a driver and loosen the set screw 44 until the protrusions 42 no longer obstruct the bone screws 16.

FIGS. 6-17 are views showing another example of an anti-backout device, or locking mechanism, of the present invention. In this example, the anti-backout device is shown being used with a bone plate, in this example, an anterior cervical plate. Like the anti-backout device described above, the anti-backout device shown in FIGS. 6-17 may also be used with any desired type of surgical implant.

Figure 6:
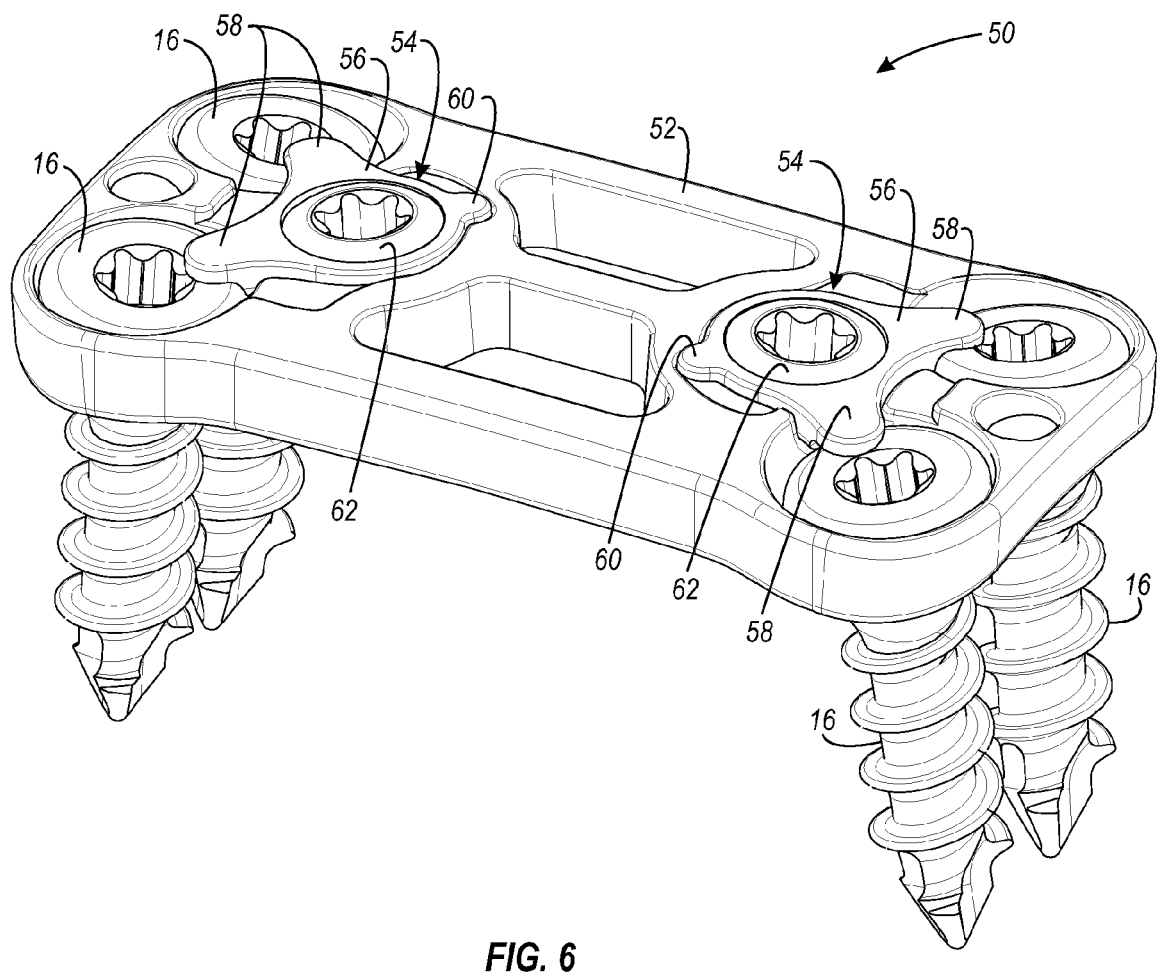
FIG. 6 is an isometric view illustrating another example of an anti-backout device of the present invention.

FIG. 6 is an isometric view showing a surgical implant. In this example, the surgical implant is an anterior cervical plate, although the anti-backout device shown in FIG. 6 may be used with any desired implant. FIG. 6 shows a surgical implant 50, including a plate 52 that is configured to be positioned over one or more bones. FIG. 6 also shows four bone screws 16 and two anti-backout devices 54, each of which are described in more detail below. The anti-backout devices 54 each include a locking plate 56 that is secured to the plate 52 by a set screw 62. If desired, the set screw 62 can include a head that will shear off when enough torque is applied by a driver, as described above with respect to FIGS. 1-5. Each locking plate 56 has two protrusions 58, which are configured to prevent the bone screws 16 from backing out when the anti-backout device is in the locked position (FIG. 6). Each locking plate 56 also has a tab 60, which helps to stop the rotation of the locking plate 56 at the appropriate position (described below).

Figure 7:
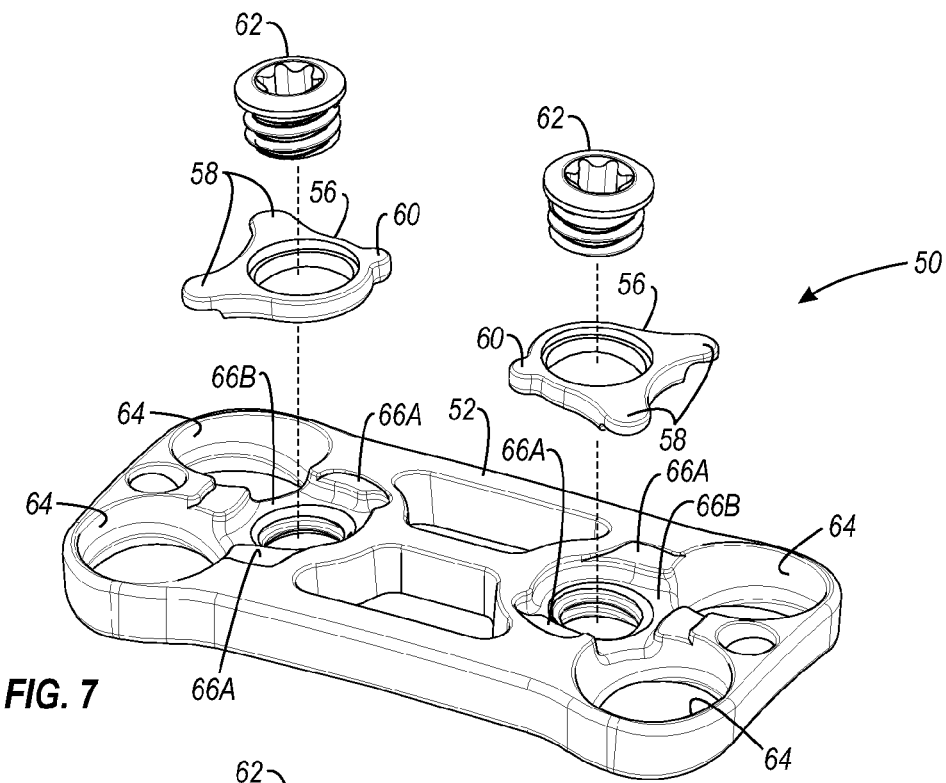
FIGS. 7 and 8 are exploded views of the anti-backout device shown in FIG. 6.
Figure 8:
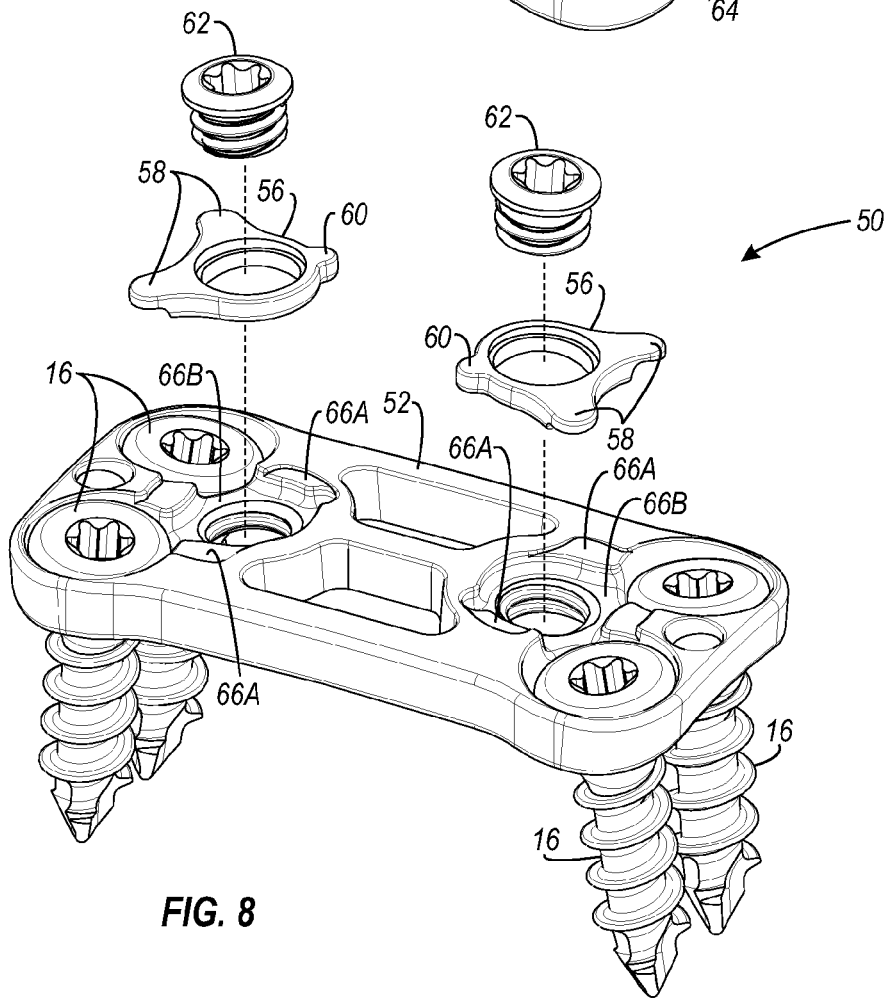

FIGS. 7 and 8 are exploded views of the surgical implant 50, showing the implant 50 (FIG. 7) and the implant 50 with four bone screws 16 installed (FIG. 8). FIGS. 7 and 8 each show the plate 52, the locking plates 56, and set screws 62.

FIG. 8 is intended to show the configurations of the bone screws 16, relative to the plate 52. Note, however, that during use, the locking plates 56 and set screws 62 can be pre-assembled with the plate 52 prior to the bone screws 16 being installed. This simplifies the use of the surgical implant for the surgeon.

In the exemplary implant 50 shown in FIGS. 6-8, four holes 64 are formed in the plate 52, and are adapted to received fasteners, such as bone screws, pegs, etc. In the example shown, the holes 64 are somewhat spherical, which allows the bone screws 16 to be inserted at an angle desired by the surgeon. The anti-backout device 54 will work regardless of the configuration of the holes 64 and the orientation of the screws 16, though.

FIGS. 6-8 illustrate details the components of the anti-backout mechanism 54. The two protrusions 58 extend outward from the locking plate 56, as shown. As shown best in FIGS. 7 and 8, the protrusions 58 are thinner than the rest of the locking plate 56, in this example. As described below, when the locking mechanism 54 is in the locked position, the protrusions 58 will not contact the screws 16. One advantage of configuring a locking mechanism such that the protrusions do not contact the screws is that it allows the screws to rotate spherically uninhibited beneath the locking mechanism (described in more detail below). In other examples, the anti-backout device can be configured so that the protrusions do contact the screws 16. The set screw 62 is configured to extend through the opening formed in the plate 56, and thread into the plate 52. A recess 66 is formed in the plate 52 that is adapted to receive its respective locking plate 56. As shown in FIGS. 7 and 8, the recess 66 has two depths. In this example, the recess has a first depth (shown at 66A) and a second deeper depth (shown at 66B). As the locking plate 56 is turned, the locking plate 56 will drop from the recess 66A and seat into the deeper recess 66B. One advantage of the invention is that a surgeon will know when the locking mechanism is locked because the surgeon will feel the locking plate 56 drop into the deeper recess while turning the set screw 62 with a driver.

The plate 52, locking plate 56, and set screw 62 can be pre-assembled, such that a surgeon will have a single implant device that includes the entire locking mechanism, rather than separately installing a locking mechanism after the implant has been installed. Once the bone screws are installed, the surgeon needs only to turn the set screw 62 with a driver to lock the bone screws in place.

Figure 9:
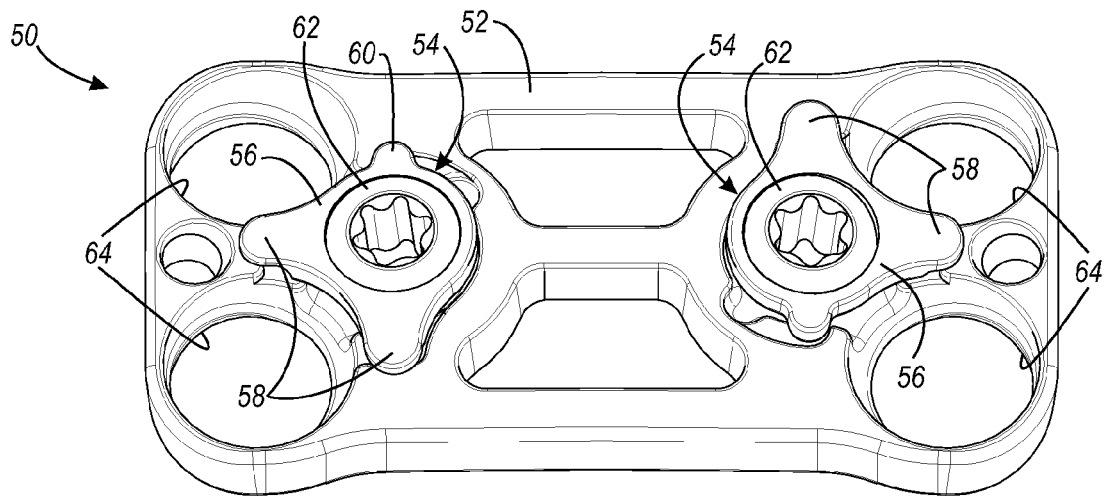
FIGS. 9-11 are isometric views of the anti-backout device shown in FIGS. 6-8, illustrating the operation of the anti-backout device.
Figure 10:
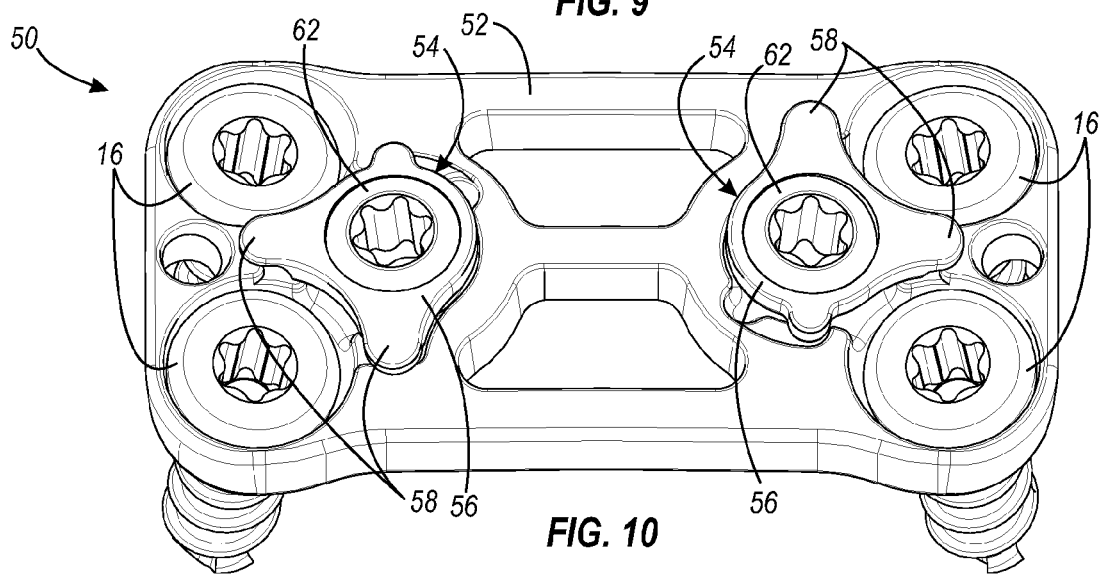
Figure 11:
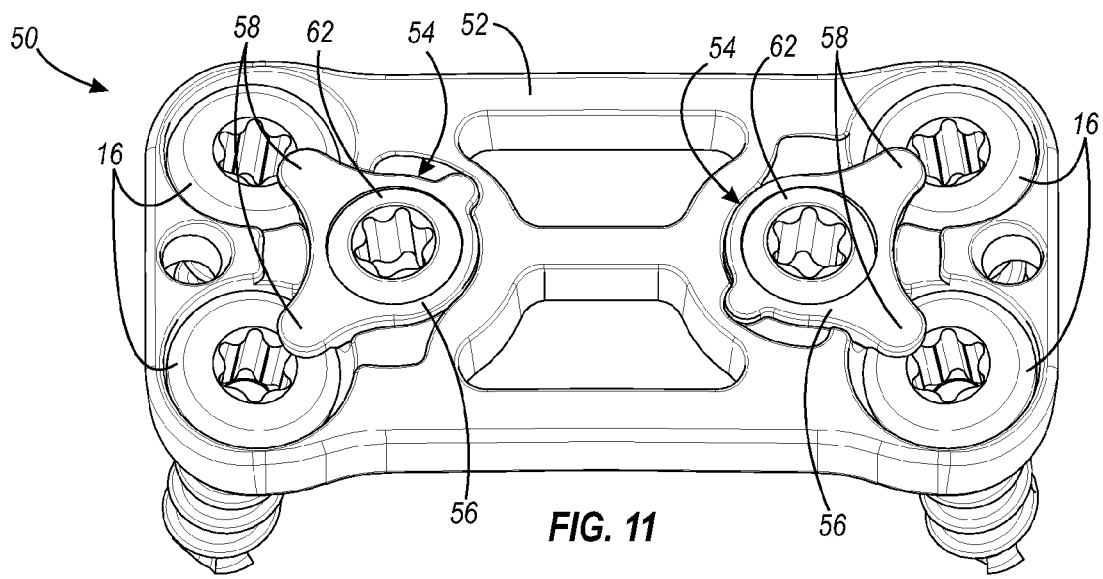

FIGS. 9-11 are isometric views of the surgical implant and anti-backout devices of the present invention, illustrating the operation of the anti-backout mechanism described above. FIG. 9 shows the implant 50, pre-assembled with anti-backout devices 54. The anti-backout devices 54 are oriented in an unlocked position, with the openings 64 unobstructed. As shown, the locking plates 56 rest on the raised recess 66A (FIGS. 7-8). When a surgeon installs the implant 50 into a patient, the plate 52 and anti-backout devices 54 can be installed all at once. FIG. 10 shows the implant 10 after the bone screws 16 have been installed. Note that the position of the protrusions 58 of the locking plate 56 are such that the openings 64 are not obstructed, allowing a surgeon to install the bone screws 16.

Once the bone screws 16 are in place, the surgeon can use a driver (in one example, the same driver that was used to install the screws 16) to turn the set screws 62. FIG. 11 shows the implant 50 after the set screws 62 have been turned. In this example, turning the set screw turned the locking plate 56 about 45 degrees clockwise, until the protrusions 58 obstruct the heads of the bone screws 16. When the locking plate 56 is in this position, the bone screws can not come out. As described above, the recess has multiple depths. As the locking plate 56 is turned, the locking plate 56 will drop from the recess 66A (FIG. 10) and seat into the deeper recess 66B (FIG. 1). Since the locking plate 56 is seated within the deeper recess 66B and held downward by the set screw 62, the locking plate 56 will not turn counterclockwise unless the set screw 62 is loosened. Also, when the tab 60 drops into the deeper recess 66B (FIG. 1), it is held in a pocket, which prevents the locking plate 56 from rotating further in either direction. The protrusions 58 prevent the screws 16 from backing out by obstructing the openings 64. In the example shown in FIGS. 6-11, a gap is formed between the protrusions 58 and the heads of the screws 16. In other examples, the protrusions 58 may contact the screws 16. Once the locking plate 56 drops into place, the set screw 62 can be tightened to a desired torque. If desired, a sheer head, similar to the head 48 shown in FIGS. 1-4 may be used. When the surgeon locks the anti-backout devices 54, the surgeon will know when the locking mechanism 54 is locked because the surgeon will feel the locking plate 56 drop into the deeper recess while turning the set screw 62 with a driver.

Figure 12:
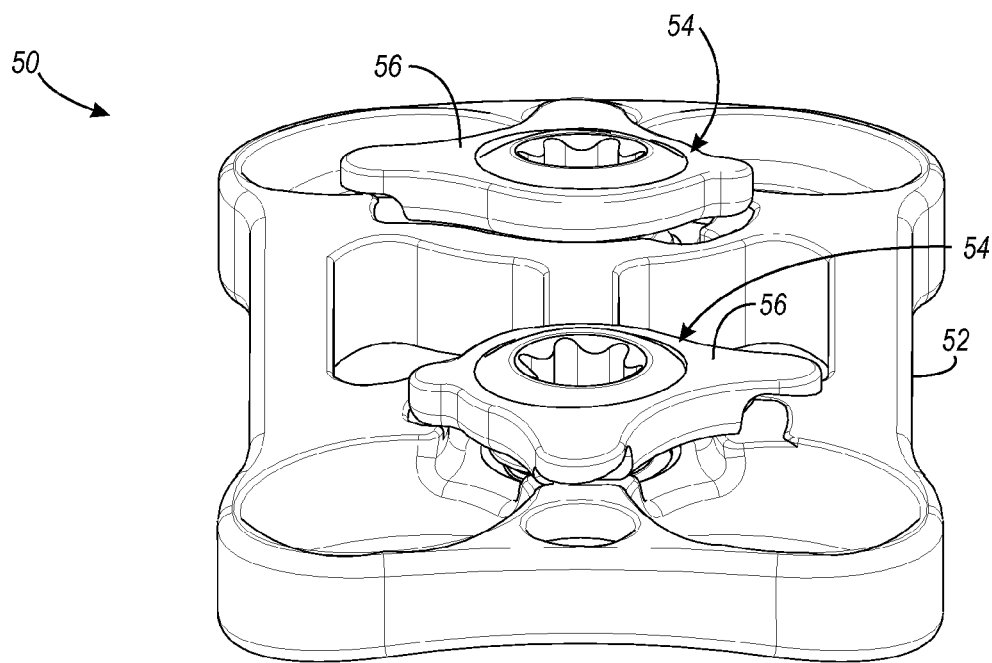
Figure 13:
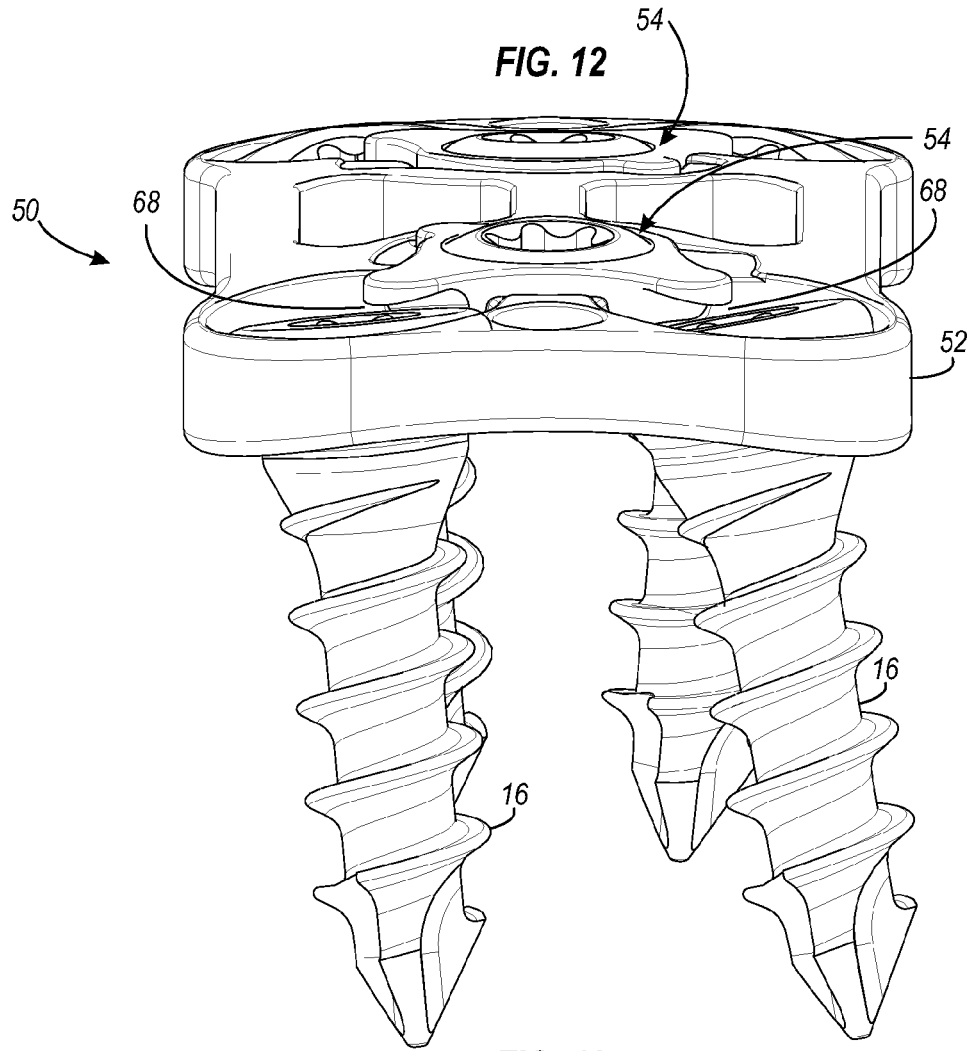

FIGS. 12-17 show various isometric views of the surgical implant 50 in locked and unlocked positions. FIGS. 12, 14, and 15 show the implant 50 in an unlocked position. FIGS. 13, 16, and 17 show the implant in a locked position. FIGS. 12, 14, and 15 shows the locking plate 56 positioned on the shallower recess 66A. In contrast, FIGS. 13, 16, and 17 show the locking plate positioned on the deeper recess 66B. These figures illustrate that the locking plate 56 drops from the recess 66A to the recess 66B when the locking mechanism is locked. FIG. 13 also illustrates that the bone screws 16 are allowed to rotate spherically, allowing a surgeon to install the bone screws 16 in any desired direction, within the range of movement of the screws. As shown in FIG. 13, when the locking mechanism 54 is in the locked position, a gap 68 is maintained between the protrusions 58 and the screws 16. This allows the screws to rotate spherically, without being inhibited by the locking mechanism.

FIGS. 18-29 are views showing another example of an anti-backout device, or locking mechanism, of the present invention. The implant shown in FIGS. 18-29 is similar to the implant shown in FIGS. 6-17, except that a single anti-backout device can be used to secure four bone screws. In this example, the anti-backout device is shown being used with a bone plate, in this example, an anterior cervical plate. Like the anti-backout devices described above, the anti-backout device shown in FIGS. 18-29 may also be used with any desired type of surgical implant.

Figure 18:
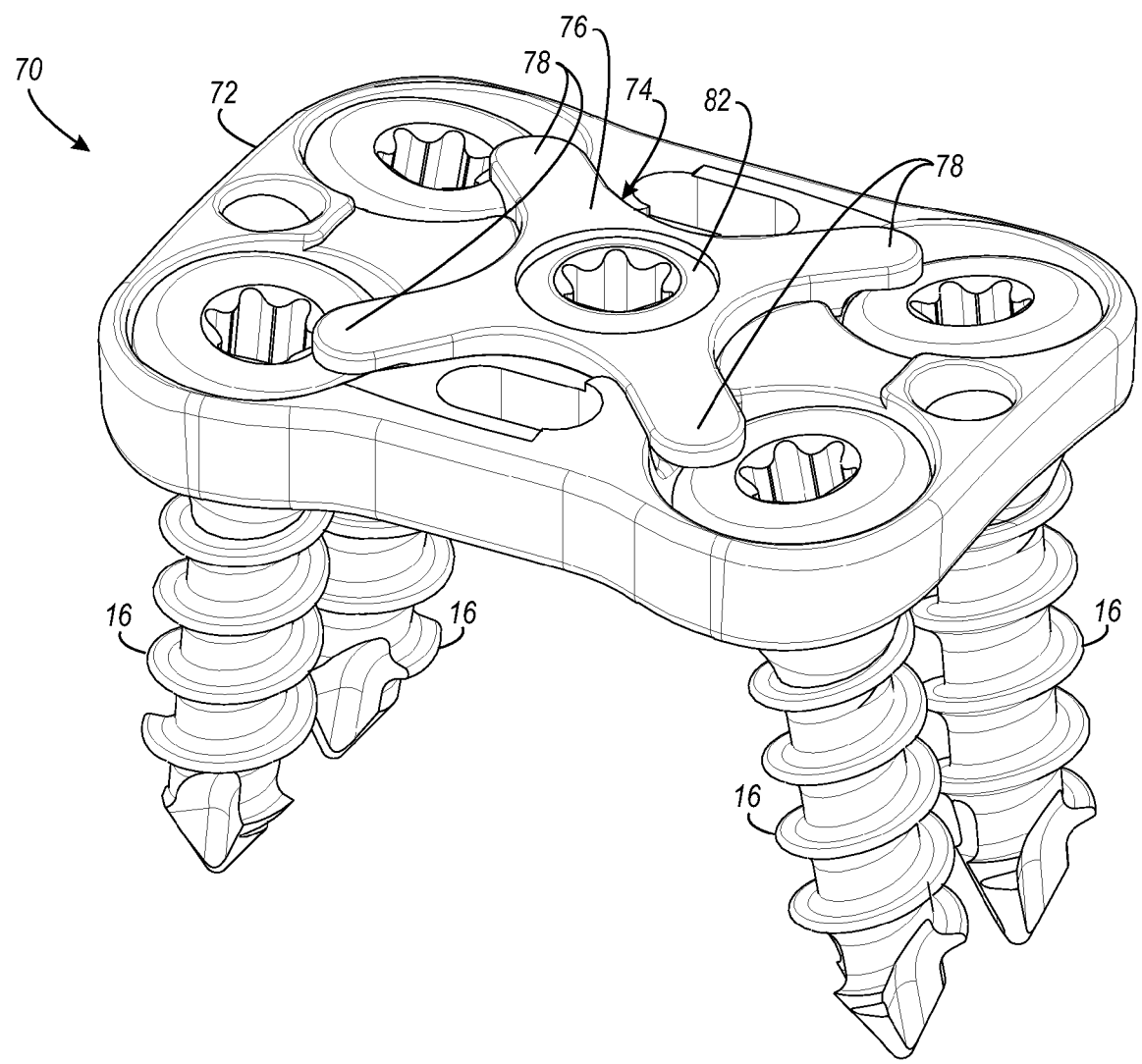
FIG. 18 is an isometric view illustrating another example of an anti-backout device of the present invention.

FIG. 18 is an isometric view showing a surgical implant 70, including a plate 72 that is configured to be positioned over one or more bones. FIG. 18 also shows four bone screws 16 and an anti-backout device 74, which is described in more detail below. The anti-backout device 74 includes a locking plate 76 that is secured to the plate 72 by a set screw 82. If desired, the set screw 82 can include a head that will shear off when enough torque is applied by a driver, as described above with respect to FIGS. 1-5. The locking plate 76 has four protrusions 78, which are configured to prevent the bone screws 16 from backing out when the anti-backout device is in the locked position (FIG. 18).

Figure 19:
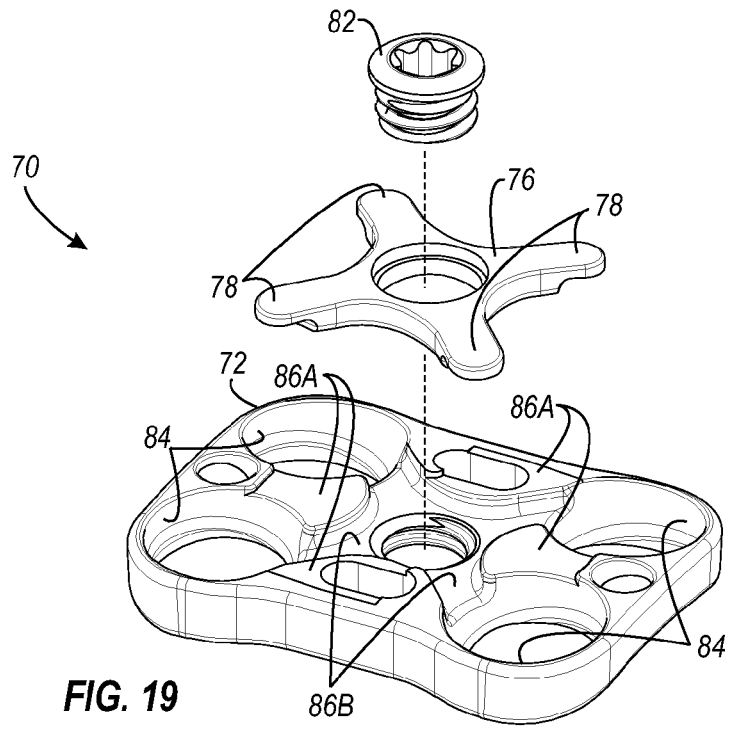
FIGS. 19 and 20 are exploded views of the anti-backout device shown in FIG. 18.
Figure 20:
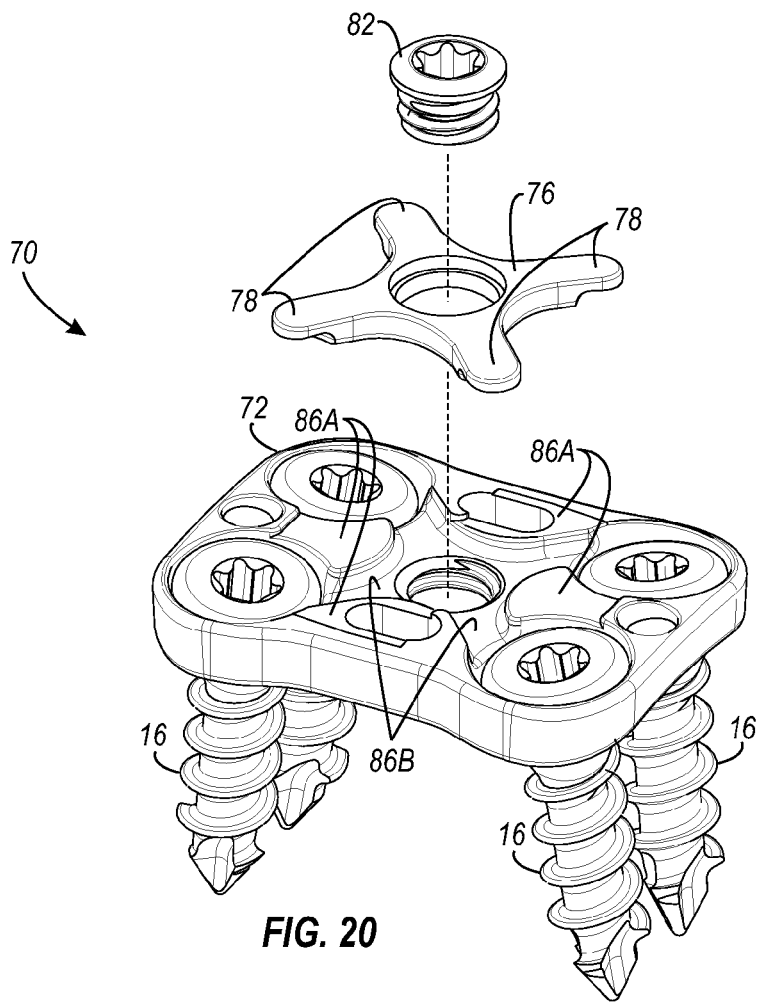

FIGS. 19 and 20 are exploded views of the surgical implant 70, showing the implant 70 (FIG. 19) and the implant 70 with four bone screws 16 installed (FIG. 20). FIGS. 19 and 20 each show the plate 72, the locking plate 76, and set screws 82. FIG. 20 is intended to show the configurations of the bone screws 16, relative to the plate 72. Note, however, that during use, the locking plate 76 and set screws 82 can be pre-assembled with the plate 72 prior to the bone screws 16 being installed. This simplifies the use of the surgical implant for the surgeon.

In the exemplary implant 70 shown in FIGS. 18-20, four holes 84 are formed in the plate 72, and are adapted to received fasteners, such as bone screws, pegs, etc. In the example shown, the holes 84 are somewhat spherical, which allows the bone screws 16 to be inserted at an angle desired by the surgeon. The anti-backout device 74 will work regardless of the configuration of the holes 84 and the orientation of the screws 16, though.

FIGS. 18-20 illustrate details the components of the anti-backout mechanism 74. The four protrusions 78 extend outward from the locking plate 76, as shown. As shown best in FIGS. 19 and 20, the protrusions 78 are thinner than the rest of the locking plate 76, in this example. As described below, when the locking mechanism 74 is in the locked position, the protrusions 78 will not contact the screws 16. One advantage of configuring a locking mechanism such that the protrusions do not contact the screws is that it allows the screws to rotate spherically uninhibited beneath the locking mechanism. In other examples, the anti-backout device can be configured so that the protrusions do contact the screws 16. The set screw 82 is configured to extend through the opening formed in the plate 76, and thread into the plate 72. A recess 86 is formed in the plate 72 that is adapted to receive its respective locking plate 76. As shown in FIGS. 19 and 20, the recess 86 has two depths. In this example, the recess has a first depth (shown at 86A) and a second deeper depth (shown at 86B). As the locking plate 76 is turned, the locking plate 76 will drop from the recess 86A and seat into the deeper recess 86B. One advantage of the invention is that a surgeon will know when the locking mechanism is locked because the surgeon will feel the locking plate 76 drop into the deeper recess while turning the set screw 82 with a driver.

The plate 72, locking plate 76, and set screw 82 can be pre-assembled, such that a surgeon will have a single implant device that includes the entire locking mechanism, rather than separately installing a locking mechanism after the implant has been installed. Once the bone screws are installed, the surgeon needs only to turn the set screw 82 with a driver to lock the bone screws in place.

Figure 21:
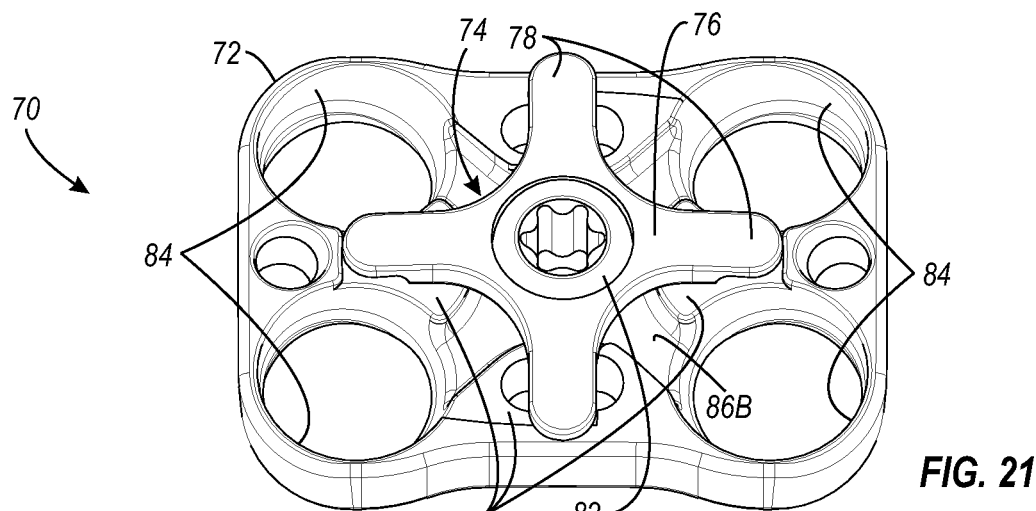
FIGS. 21-23 are isometric views of the anti-backout device shown in FIG. 18, illustrating the operation of the anti-backout device.
Figure 22:
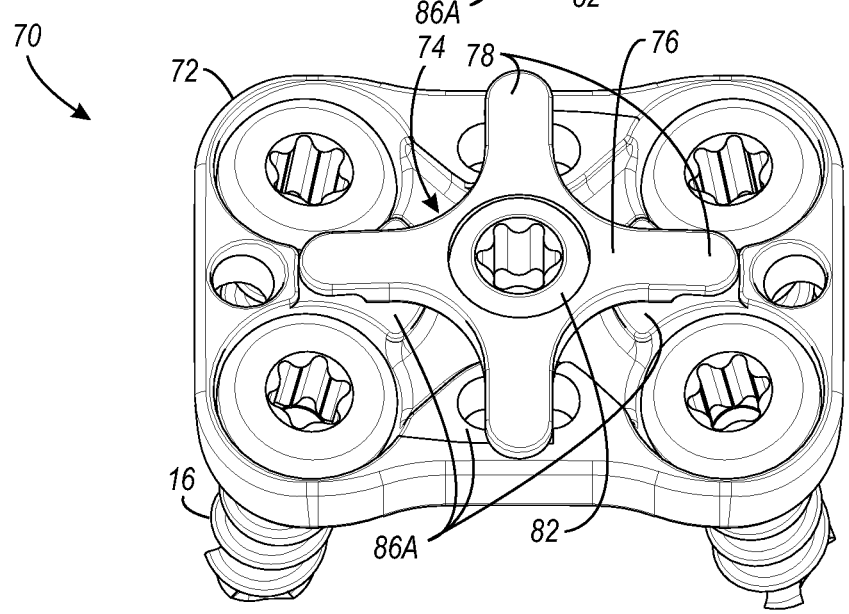
Figure 23:
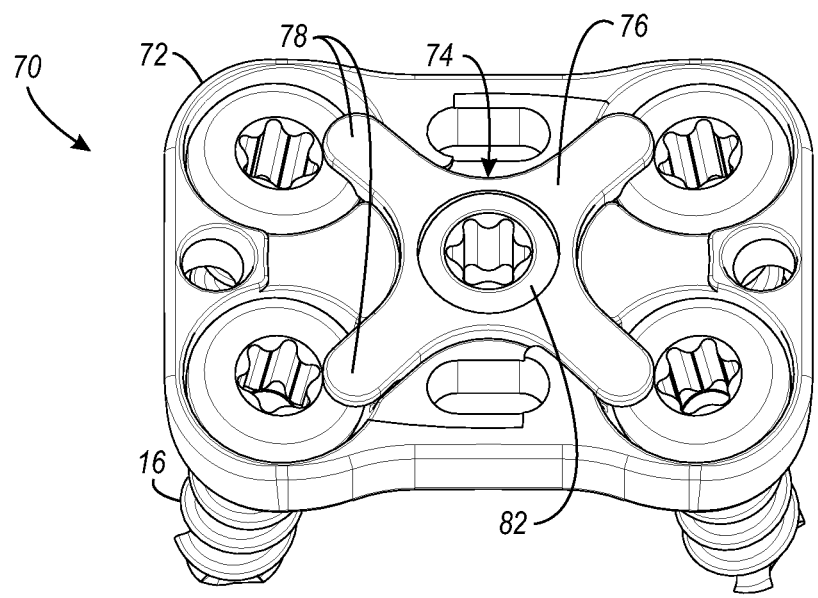

FIGS. 21-23 are isometric views of the surgical implant and anti-backout device of FIGS. 18-20, illustrating the operation of the anti-backout mechanism. FIG. 21 shows the implant 70, pre-assembled with anti-backout device 74. The anti-backout device 74 is oriented in an unlocked position, with the openings 84 unobstructed. As shown, the locking plate 76 rests on the raised recess 86A (FIGS. 19-20). When a surgeon installs the implant 70 into a patient, the plate 72 and anti-backout device 74 can be installed all at once. FIG. 22 shows the implant 10 after the bone screws 16 have been installed. Note that the position of the protrusions 78 of the locking plate 76 are such that the openings 84 are not obstructed, allowing a surgeon to install the bone screws 16.

Once the bone screws 16 are in place, the surgeon can use a driver (in one example, the same driver that was used to install the screws 16) to turn the set screw 82. FIG. 23 shows the implant 70 after the set screw 82 has been turned. In this example, turning the set screw 82 turns the locking plate 76 about 45 degrees clockwise, until the protrusions 78 obstruct the heads of the bone screws 16. When the locking plate 76 is in this position, the bone screws 16 can not come out. As described above, the recess 86 has multiple depths. As the locking plate 76 is turned, the locking plate 76 will drop from the recess 86A (FIG. 22) and seat into the deeper recess 86B (FIG. 23). Since the locking plate 76 is seated within the deeper recess 86B and held downward by the set screw 82, the locking plate 76 will not turn counterclockwise unless the set screw 82 is loosened. The protrusions 78 prevent the screws 16 from backing out by obstructing the openings 84. In the example shown in FIGS. 18-23, a gap is formed between the protrusions 78 and the heads of the screws 16. In other examples, the protrusions 78 may contact the screws 16. Once the locking plate 76 drops into place, the set screw 82 can be tightened to a desired torque. If desired, a sheer head, similar to the head 48 shown in FIGS. 1-4 may be used. When the surgeon locks the anti-backout device 74, the surgeon will know when the locking mechanism 74 is locked because the surgeon will feel the locking plate 56 drop into the deeper recess while turning the set screw 82 with a driver.

Figure 24:
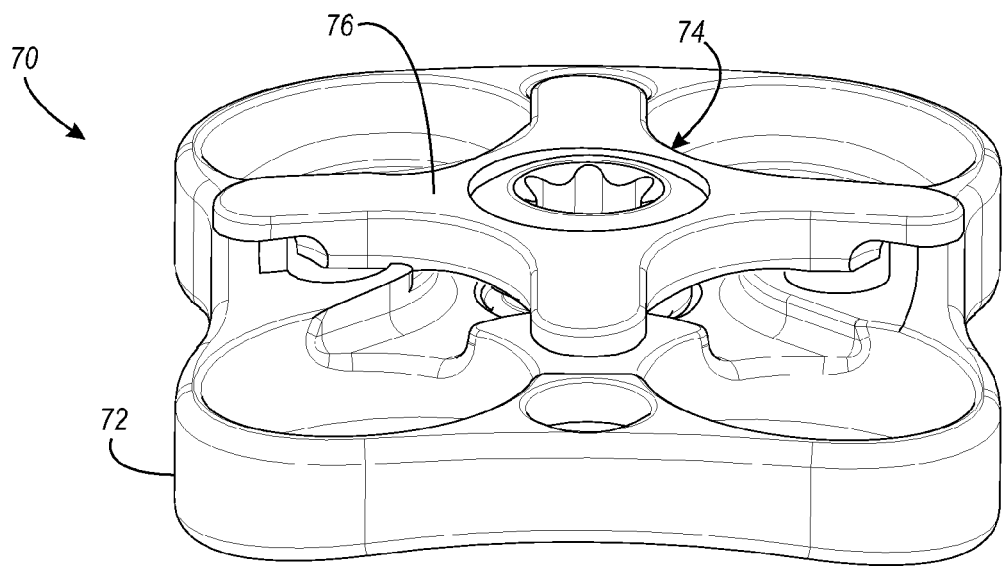
FIGS. 24-29 show various isometric views of the surgical implant of FIG. 18 in locked and unlocked positions.
Figure 25:
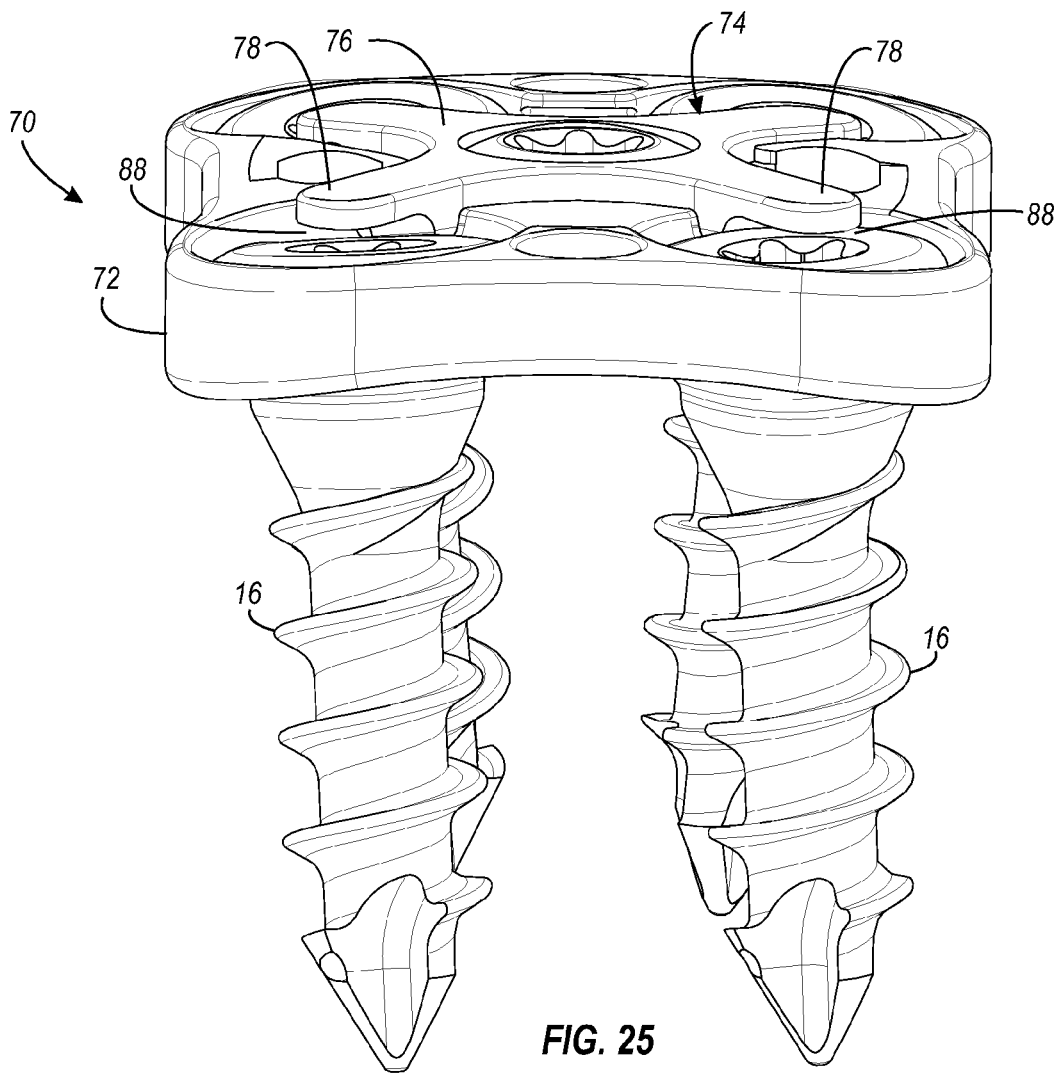
Figure 26:
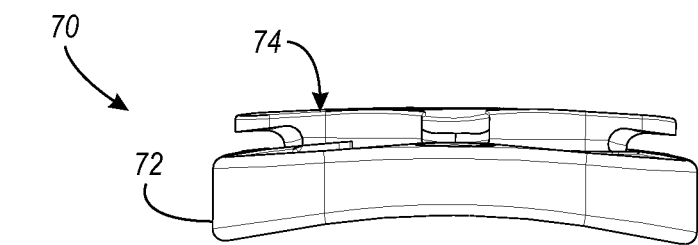
Figure 27:
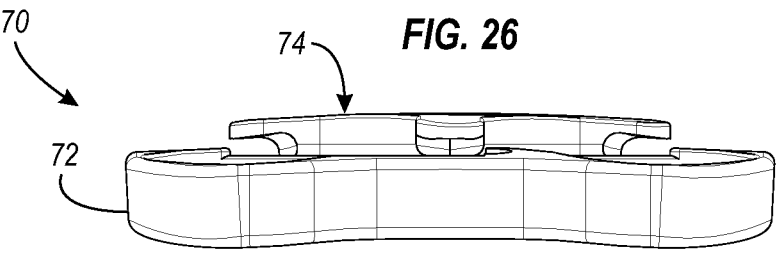
Figure 28:
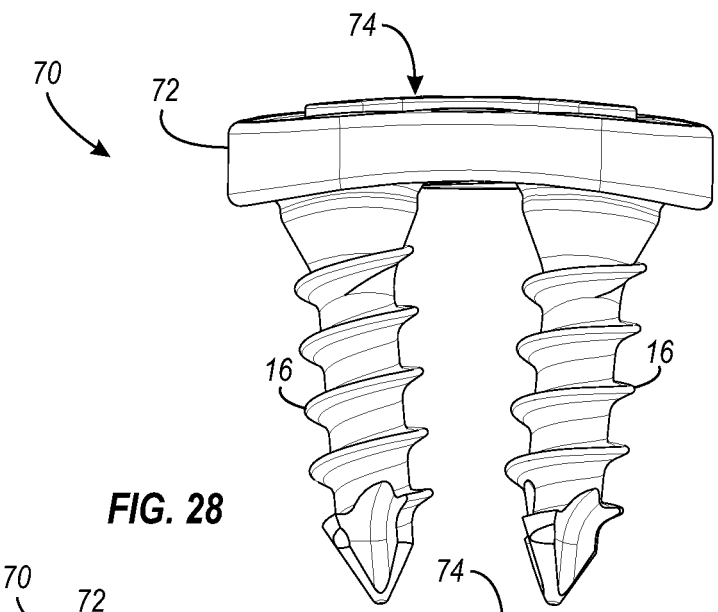
Figure 29:
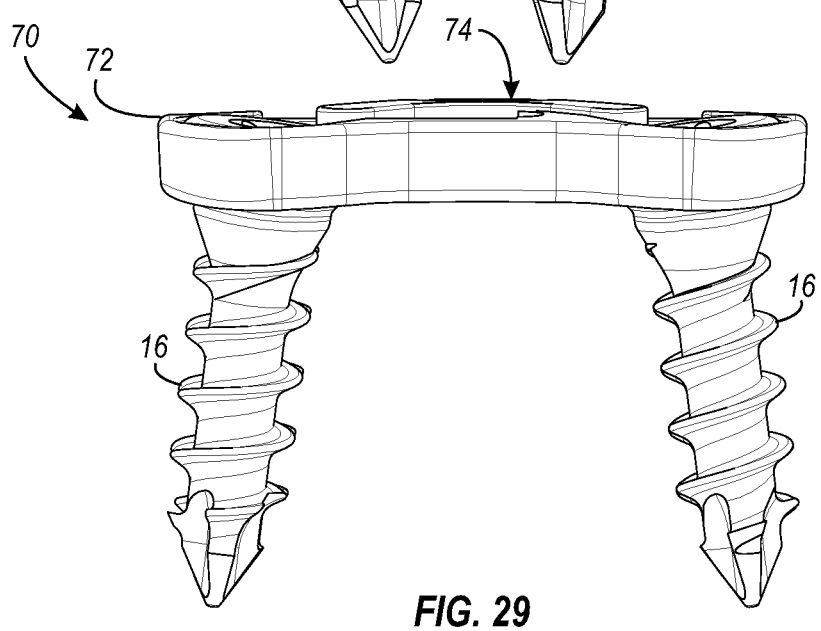

FIGS. 24-29 show various isometric views of the surgical implant 70 in locked and unlocked positions. FIGS. 24, 26, and 27 show the implant 70 in an unlocked position. FIGS. 25, 28, and 29 show the implant in a locked position. FIGS. 24, 26, and 27 shows the locking plate 76 positioned on the shallower recess 86A. In contrast, FIGS. 25, 28, and 29 show the locking plate positioned on the deeper recess 86B. These figures illustrate that the locking plate 76 drops from the recess 86A to the recess 86B when the locking mechanism is locked. As shown in FIG. 25, when the locking mechanism 74 is in the locked position, a gap 88 is maintained between the protrusions 78 and the screws 16. This allows the screws to rotate spherically, without being inhibited by the locking mechanism.

Figure 30:
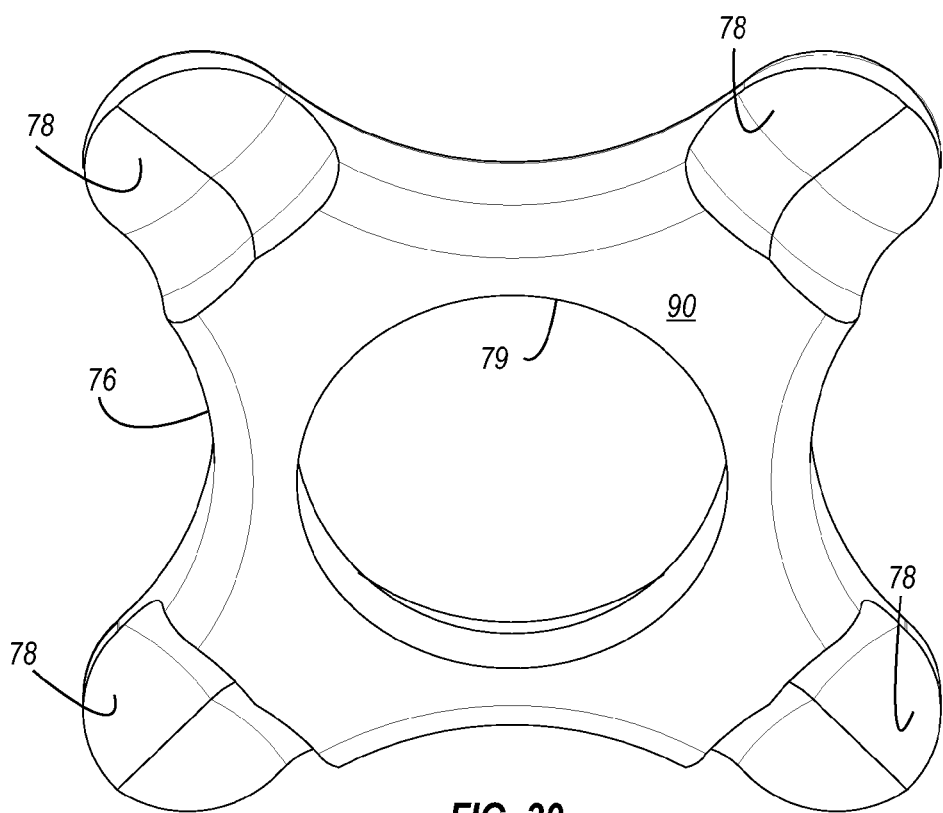
FIGS. 30-31 are isometric diagrams illustrating two examples of locking plates of the present invention.
Figure 31:
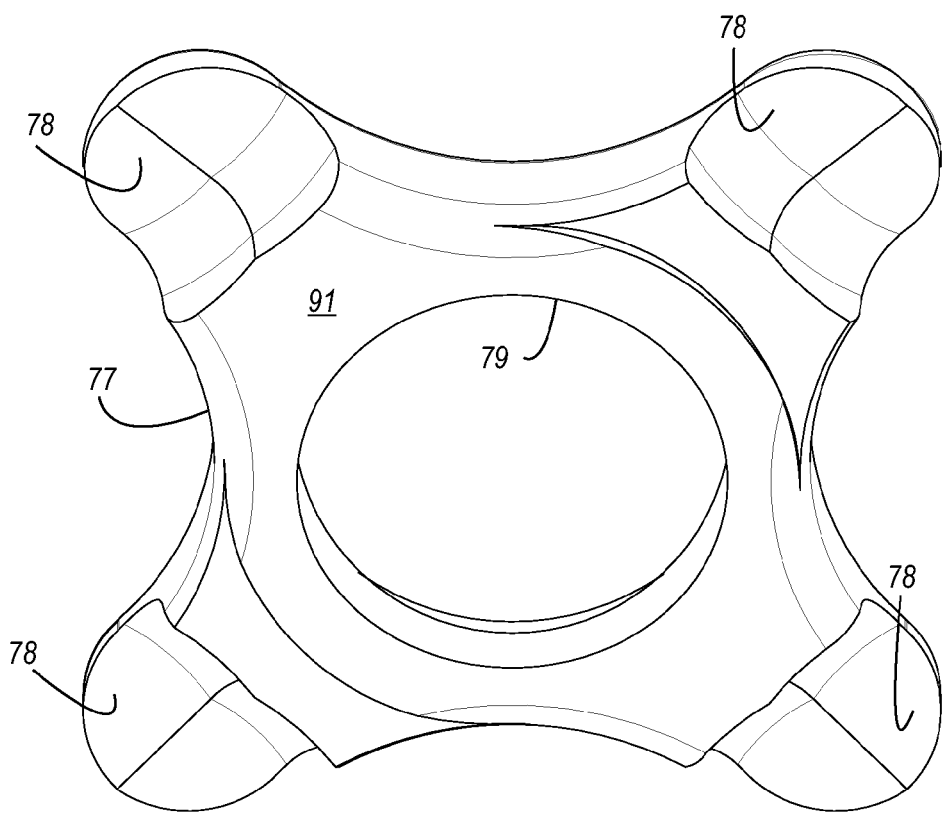

FIGS. 30-31 are isometric diagrams illustrating two examples of locking plates of the present invention. FIG. 30 is an isometric diagram of the locking plate 76 shown in FIGS. 18-29. The locking plate 76 has four protrusions 78, as described above, with an opening 79 formed to receive a set screw 82. The locking plate 76 has a substantially flat bottom surface 90, which is adapted to sit on the shallow and deep recesses 86A and 86B (described above). When a surgeon turns the set screw, friction between the set screw and the surfaces of the opening 79 will tend to cause the locking plate 76 to turn with the set screw. Until the locking plate 76 drops down to the deeper recess 86B, the bottom surface 90 contacts the recess 86A. As long as friction between the set screw 82 and the locking plate 76 is greater than the friction between the locking plate 76 and the recess 86A, the locking plate 76 should turn with the set screw 82.

Various design considerations determine how easily the locking plate will rotate, relative to the bone plate 72. Materials or coatings on the locking plate 76 and bone plate 72 will affect the amount of friction that there is between the locking plate 76 and bone plate 72. Therefore, if less friction is desired (e.g., if the set screw tightens without the locking plate rotating), the locking plate 76 and/or bone plate 72 can be made of materials, or coated with materials, with a lower coefficient of friction, and visa versa. In one example, the bone plate and locking plate are made of Titanium. Another design consideration that affects the amount of friction between the locking plate and bone plate is the amount of surface area of the locking plate that contacts the recess 86A. FIG. 31 is an isometric diagram of a locking plate 77 having bottom surface 91 that has less surface area compared to the bottom surface 90 of the locking plate 76 shown in FIG. 30. Since there will be less surface area contacting the recess 86A, there will be less friction, and the locking plate 77 will turn more easily than the locking plate 76 shown in FIG. 30. Alternately, the surface area of the recess 86A could be reduced to reduce the friction between the locking plate and the bone plate. In another example, the bottom surface of the locking plate and/or the surface of the bone plate can be angled such that the locking plate will turn easier, relative to the bone plate. It can be seen that, the resistance experienced when rotating a locking plate can be controlled by configuring various aspects of the locking plate and bone plate.

Various other configurations and embodiments of anti-backout mechanisms are also possible within the spirit and scope of the invention. Also, exemplary the anti-backout mechanisms described above can be used in combination with each other. For example, one a single medical implant, a locking mechanism 54 (e.g., FIG. 6) and a locking mechanism 74 (e.g., FIG. 18) can be used to secure fasteners.

As mentioned above, a locking mechanism of the present invention can be pre-assembled with an implant (e.g., FIGS. 1, 9, 21), making the use of the implant and locking mechanism easier. However, if an implant and locking mechanism are pre-assembled, it will be desired that the locking mechanism does not rotate during transit or storage.

Figure 32:
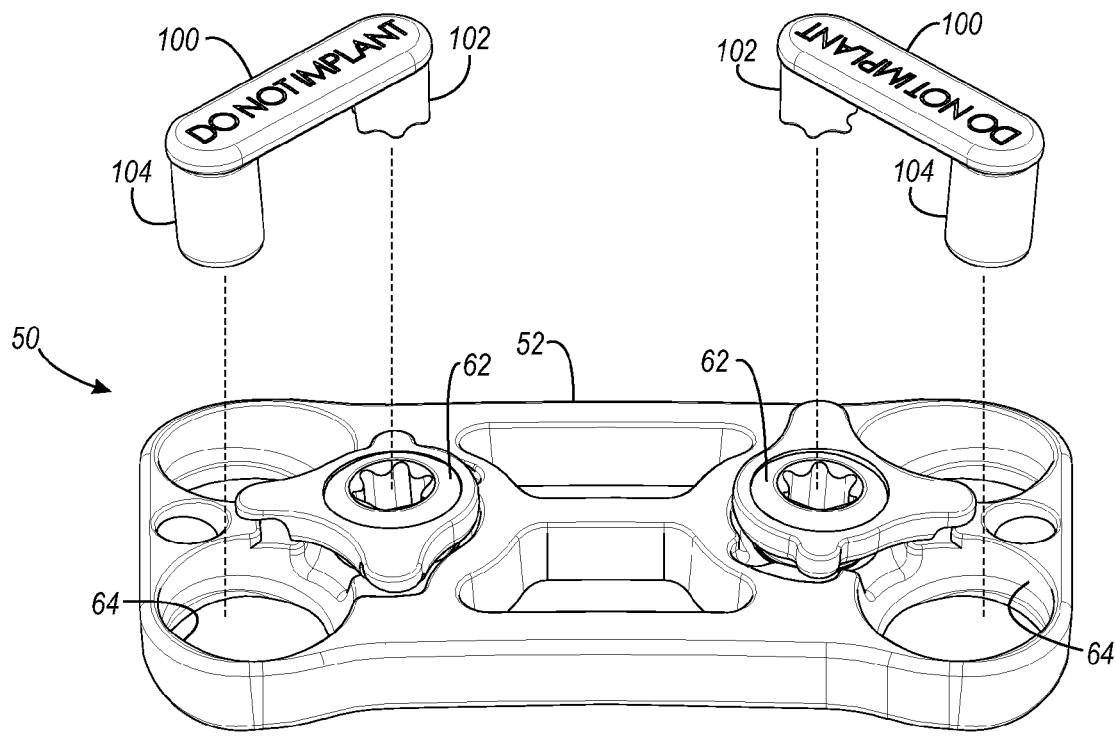
FIGS. 32-33 are isometric views showing an implant and retention devices of the present invention.
Figure 33:
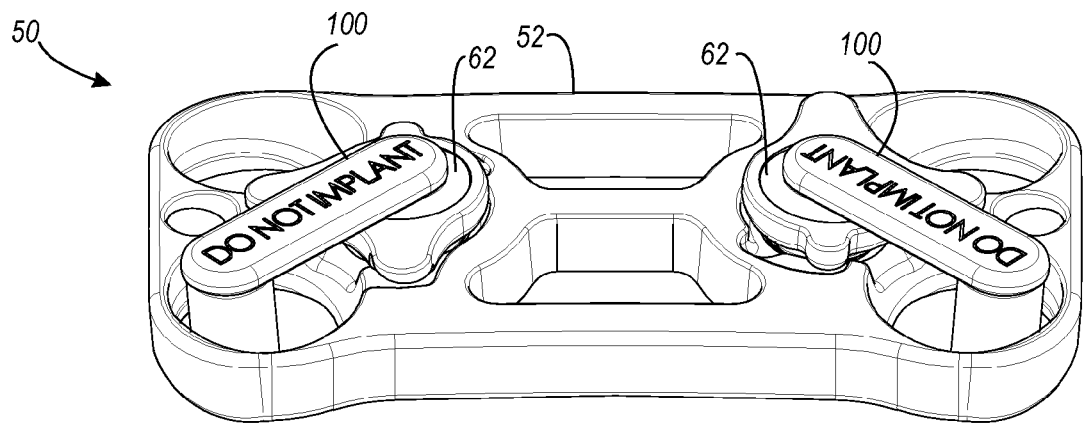

FIGS. 32-33 are isometric views showing an implant and retention devices of the present invention. FIG. 32 is an exploded isometric view showing an implant 50, as described above. FIG. 32 also shows two retention devices 100, which are configured to keep the implant 50 in an assembled position by preventing the set screws from turning prior to the use of the implant. When a surgeon is ready to install the implant, the surgeon can simply remove the retention devices 100 from the implant 50. In the example shown, the retention device 100 has a plug 102 shaped to fit into the star driver head (e.g., a Torx™ head) of the set screw 62. Coupled to the plug 102 is a pin 104 that is configured to engage the implant in such a way that the plug 102 will keep the set screw 62 from rotating. FIG. 33 shows the implant 50 and retention devices 100 in an assembled view. In this example, the plug 102 is configured to fit into one of the opening 64 formed in the plate 52. In other examples, the retention device can engage other openings or surfaces of the implant. In another example, the pin 104 can be configured like the plug 102 and fit into the star head of the other set screw, thus only requiring only one retention device 100 per implant.

Figure 34:
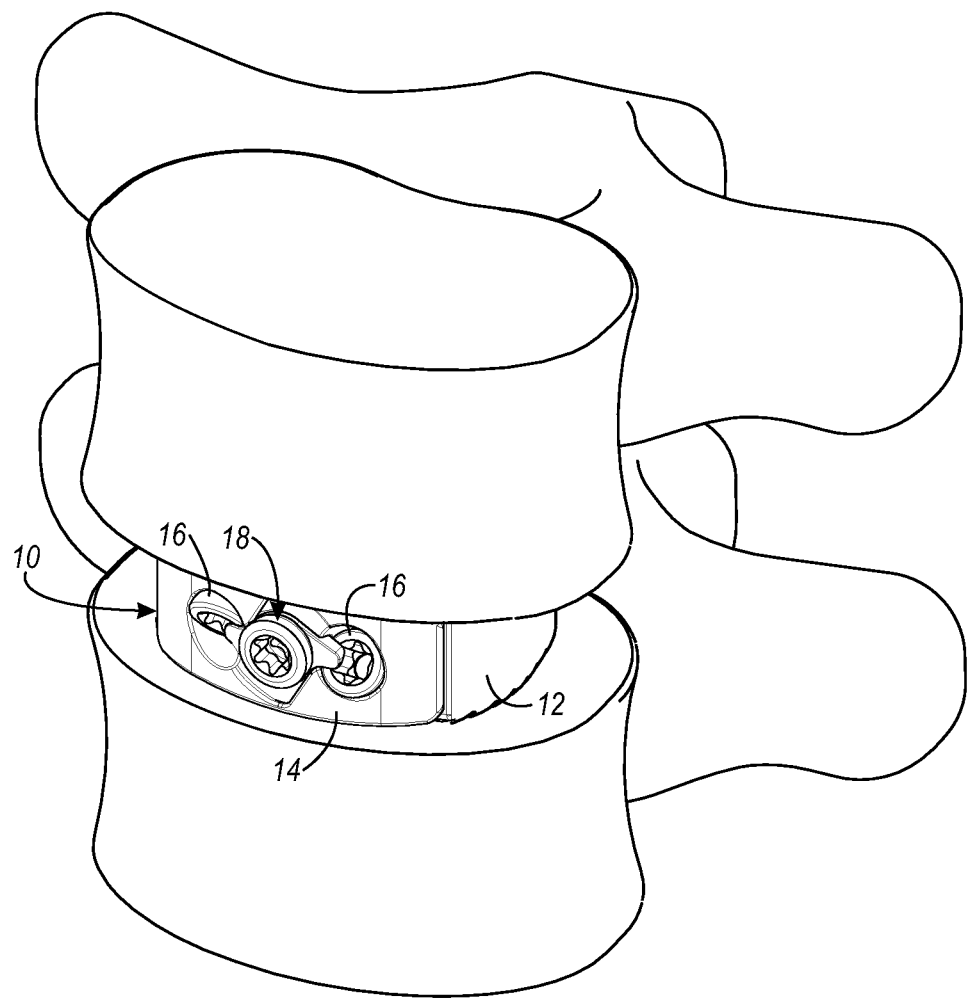
FIG. 34 is an isometric diagram of the implant shown in FIG. 1, installed between the end plates of two adjacent vertebrae.

Another feature of the present invention relates to an anti-backout device that is capable of securing two or more fasteners that are installed into two or more separate bones. FIG. 34 is an isometric diagram of the implant shown in FIG. 1, installed between the end plates of two adjacent vertebrae. As shown, when installed, one bone screw 16 is screwed into one vertebrae, and the other bone screw 16 is screwed into the other vertebrae. In the example shown in FIG. 34, the left screw 16 is angled upward and screwed into the upper vertebrae and right screw 16 is angled downward and screwed into the lower vertebrae. Although the two bone screws 16 are secured to two separate bones, the locking mechanism 18 is capable of locking both screws 16.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A medical device comprising:
    an interbody fusion implant comprising a load bearing device and an anterior retention device configured to couple to the load bearing device;
    one or more fasteners configured to secure the implant in an implanted position;
    a recess formed in the implant anterior retention device, wherein the recess is adapted to receive a movable device, and wherein a portion of the recess has a first depth and a portion of the recess has a second depth and wherein the second depth is deeper than the first depth;
    a movable device coupled to the implant anterior retention device, the movable device having a locked position and an unlocked position, wherein, in the unlocked position, the movable device is disposed within the portion of the recess having the first depth and in the locked position, the movable device is disposed within the portion of the recess having the second depth and further wherein the movable device is capable of being rotationally turned and the movable device drops from the portion of the recess having the first depth to the portion of the recess having the second depth when the movable device is rotationally turned; and
    one or more protrusions extending from the movable device, wherein the one or more protrusions are configured to prevent migration of the one or more fasteners when the movable device is in the locked position and wherein each of the one or more protrusions contacts one of the fasteners when the movable device is in the locked position; and
    a set screw for securing the movable device in the locked position wherein the set screw includes a shear head coupled to the set screw and wherein the shear head is configured to break apart from the set screw when sufficient torque is applied to the shear head.

2. The device of claim 1, wherein the set screw and movable device is pre-assembled with the implant prior to use.

3. The medical device of claim 1, wherein each of the one or more protrusions does not contact the one or more fasteners when the movable device is in the unlocked position.

* * * * *